United States Patent [19]

Banks

[11] Patent Number: 4,814,060
[45] Date of Patent: Mar. 21, 1989

[54] ION SELECTIVE ELECTRODES AND METHOD OF MAKING SUCH ELECTRODES

[75] Inventor: Rodney H. Banks, Naperville, Ill.

[73] Assignee: Nalco Chemical Company, Naperville, Ill.

[21] Appl. No.: 182,422

[22] Filed: Apr. 18, 1988

[51] Int. Cl.[4] ............................................. G01N 27/30
[52] U.S. Cl. .................................... 204/406; 204/412; 204/414; 204/418
[58] Field of Search ............... 204/418, 414, 412, 406; 128/635; 357/25

[56] References Cited

U.S. PATENT DOCUMENTS 3,923,627  12/1975  Niedrach et al. ............... 204/418 X
4,568,445  2/1986  Cates et al. ........................ 204/415

Primary Examiner—G. L. Kaplan
Attorney, Agent, or Firm—Kinzer, Plyer, Dorn, McEachran & Jambor

[57] ABSTRACT

An ion selective microelectrode in which the reference solution is an aqueous solution of formamide (or methyl formamide) and in which the ionophore-containing membrane covering the reference solution is PVC dissolved in water-insoluble 3-methylcyclohexanone (or equivalent substituted cyclic ketone). The reference solution may be gelled with PVA and preferably is buttressed to assure against incursion of membrane components.

18 Claims, 1 Drawing Sheet

ION SELECTIVE ELECTRODES AND METHOD OF MAKING SUCH ELECTRODES

BACKGROUND OF THE INVENTION

Commercial ion selective electrodes (ISE) are a class of chemical sensors that are presently expensive, fragile, bulky, and require periodic maintenance. There is considerable ISE research being done to miniaturize them, and in so doing, make them more rugged, less expensive, and in some cases even disposable. There are many technology areas that can greatly benefit from these improved ISE devices such as the medical field, environmental chemistry, analytical chemistry, process analytical chemistry, and the chemical manufacturing industry. With the development of microsensors, arrays of multiple sensors can be made quite easily and cheaply. These arrays can be incorporated into on-line process analyzers, giving them increased reliability, accuracy, capability, and cost effectiveness. Maintenance costs would be minimized if they can be made disposable. In the medical and clinical fields, the chemistry of individual cells can be studied and the ionic composition of a patient's blood can be monitored on-line during surgery.

Progress in the development of stable micro ISE devices has been hampered by several fundamental problems. Commercial electrodes have a built-in stabilizing internal reference system based on either Ag/AgCl reference elements immersed in aqueous reference solutions or an inert platinum (or gold) wire immersed in an aqueous solution containing a redox couple. Without this internal reference system, the potential of the electrode drifts, decreasing the accuracy of the measurement and requiring frequent calibration.

Most commercial liquid membrane ISE devices have an ion sensitive membrane in direct contact with the internal reference solution. In making this electrode, the membrane is formed first, sealed to the electrode body, then it is filled with the internal reference solution. This method is not easily miniaturized.

The simplest way to miniaturize an ISE device is to eliminate the internal reference system and put the membrane in direct electrical contact with the conductor. Microelectrodes of the coated wire type (CWE), obtained by coating a wire with an ion sensitive membrane, are commonly reported in the literature as being quite functional, but suffer potential drift on the order of mV/hr; see "Coated-Wire Ion-Selective Electrodes" in Ion-Selective Rev. 1984, Vol. 6, pp 125–172; Pergamon Press Ltd. Electrodes having an internal reference system show drifts of uV/hr or less.

Chemical microsensors called ISFET's (Ion Sensitive Field Effect Transistor) are made by directly attaching an ion sensitive membrane to the gate of an FET. Besides being very small (about 2mm$^2$) the microsensor chip is inexpensive, rugged, and is of low output impedance. Again, due to the lack of an internal reference system, these devices are subject to potential drifts.

It is apparent that one cannot simply scale down a conventional ISE since, at small dimensions, it is difficult to attach a membrane due to the small volume. Water evaporation through the membrane is significant. Complete loss of the internal reference solution occurs in a few days, depending on membrane thickness, rendering the device inoperable.

There are numerous papers and patents describing attempts to build an internal reference system into micro devices. For CWE, a polyvinyl alcohol (PVA) gel containing KCl was used, over which the membrane was cast; see "Miniature Solid State Potassium Electrode for Serum Analysis" in Analytical Chemistry, Vol. 45, No. 9, Aug. 1973. It was noted in this paper that special care was needed in order to prevent the membrane from bursting. The patent literature presents disclosures of small electrodes having a "dried" internal reference system which becomes active when moisture diffuses into it through the outer membrane: U.S. Pat. Nos. 3,856,649; 4,214,968; 4,340,457; 4,487,679; 4,571,293; 4,578,173; and 4,615,788. At best these systems seem marginally effective.

THE PRESENT INVENTION: SUMMARY

Figure 1:
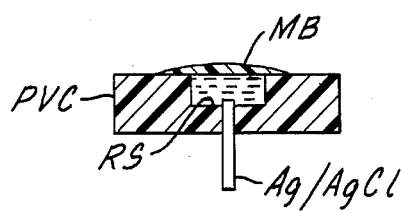
FIGS. 1–9 are simplified views of various electrode constructions and configurations in accordance with the present invention.

The present disclosure may be introduced by consideration of two main parts, each of which addresses a problem in making stabilized micro ISE devices. The first part concerns the development of an internal reference solution that will not evaporate through the membrane. The second part involves a composition of membrane casting solution that can be directly applied over the internal reference solution without development of flaws. Both of these are combined to make a micro ISE in accordance with the present invention.

Formamide-based Internal Reference Solution (Part 1)

The optimum internal reference solution under the present invention will have the following properties:
 (a) will not evaporate through the membrane; compared to $H_2O$, will have a higher boiling point and be liquid at normal operating temperatures;
 (b) has a dielectric constant 80 so salts will dissolve, giving ions;
 (c) miscible with $H_2O$;
 (d) insoluble in nonpolar organics;
 (e) generally chemically inert under normal operating conditions.

Formamide, $HCONH_2$, (F) satisfies the above requirements. It was found that for best performance, a formamide $H_2O$ solution should be used; a ratio of 80/20 to 90/10 F/$H_2O$ is optimum but in extreme cases the ratio may be 100/0 to 50/50. Formamide is hygroscopic so the addition of water stabilizes this tendency.

A typical internal reference solution constituted by formamide is:
 80–90% by weight formamide;
 10–20% by weight $H_2O$;
 0.001–0.1M salt of the ion to be determined, for example $CaCl_2$ for Ca electrode. NaCl can be used for both pH and anion electrodes;
 sufficient $AgNO_3$ to saturate the reference solution with AgCl.

Optional ingredients are:
 High molecular weight PVA (polyvinyl alcohol) to give a gelled internal reference solution. Usually 3–6% by weight PVA performs satisfactorily, but lesser amounts may be used.
 As will be seen later, to help increase lifetime and reduce leaching of active membrane components into the internal reference solution, the formamide-based internal reference solution can be saturated with the ionophore and a plasticizer. This requires very small amounts.

The Ag/AgCl internal reference element can be made by the standard methods of electrical anodization or chemical oxidation. The Ag/AgCl element may be a silver wire, vapor deposited silver metal, silver epoxy or silver inks applied to a plastic wire.

Redox-based systems can also be used, for example, using a $K_4Fe(CN)_6/K_3Fe(CN)_6$ system: see U.S. Pat. No. 4,214,968, columns 11 and 12. In this case the formamide based internal solution may have the general composition:

80–90% formamide
10–20% $H_2O$
0.05M $K_4Fe(CN)_6$
0.05M $K_3Fe(CN)_6$
0.05M KCl The value of, 0.05M for the cyanide (redox) compounds is not a critical value as long as both are at about the same concentration. The 0.05M KCl salt is for a K+ electrode for example.

When a redox couple is present the element is an inert metal, platinum or gold; systems of this kind were tested with good results.

Membrane Casting Solution (Part 2)

Before a detailed discussion of the present casting solution is set forth, it is helpful to understand prior practice, now to be briefly described.

All membrane casting solutions are based on polyvinyl chloride (PVC) plastic that is dissolved in tetrahydrofuran (THF) or cyclohexanone (CH) solvent. Also contained are the active components that make the final membrane ion sensitive, particularly the ionophore. A typical casting solution (weight %) comprises the following:

1–2% ionophore - responsible for ion sensitivity
32–34% PVC powder
0.1–0.7% $KB(Cl-Ph)_4$ or $NaB(Ph)_4$
63–67% plasticizer, e.g. nitrophenyl octyl ether
Enough THF or CH solvent to dissolve all components and make a viscous solution Over 90 percent of the casting solutions described in the literature use THF and the remainder use CH. THF is miscible with water and CH is soluble in water, between 150 g/l to 50 g/l, from 10° C.–30° C.

For large electrodes of conventional construction, the membranes are precast before coming in contact with the reference solution; see "PVC Matrix Membrane Ion-Selective Electrodes" in Journal of Chemical Education, Vol. 51, No. 8, Aug. 1974. From FIG. 3 of this reference it is apparent that it would be difficult to seal on a rubbery, somewhat sticky membrane measuring about 1 mm diameter onto a plastic tube and fill the tube with solution with not air bubbles and then to insert and seal the reference element.

Without an aqueous internal reference solution, the PVC solution can be directly applied to the conductor; see "Procedure for the Construction of All-Solid-State PVC Membrane Electrodes" in ANALYST July 1986, Vol. III. This method is much more readily adaptable to making micro ISE devices as can be imagned from FIG. 1 of this last reference which also mentions a relatively poor long term stability with this type of design.

Since THF and CH solvents are readily water soluble they cannot be directly applied over an aqueous or formamide-based internal reference solution since mixing will occur and a cloudy, poorly formed, nonfunctional membrane will result. It may also develop pinholes.

All other membrane casting solution components are highly water insoluble. Consequently, I perceived the advantages to be achieved by a membrane casting solvent which will dissolve PVC, which is water insoluble, and, optimally, has a density of less than 1 so it will not have a tendency to sink into the internal reference solution but will float.

The preferred solvent to dissolve PV in accordance with the present invention is 3-methylcyclohexanone (3-MCH) but other substituted cyclic ketones also perform such as dimethylcyclohexanone or dimethylcycloheptanone, etc. The higher substituted materials have lower evaporation rates which is a disadvantage and consequently 3-methylcyclohexanone is deemed optimum.

A calcium electrode was made using a gelled formamide-based internal reference solution. The casting solution was prepared with 3-MCH as the solvent for PVC. The casting solution was directly applied over the gel. A diagram of the electrode is shown in FIG. 1 where the PVC plate or support is ¼" thick, RS is the reference solution and MB is the membrane. The support could also be polystyrene or polycarbonate.

Initial testing showed good results. After several days soaking in the sample solution, it lost activity because the membrane was too thin and the active membrane components were leached out by the sample solution. Its activity was readily restored by building up the membrane thickness by a few more drops.

Thus, by properly applying sufficient drops of casting solution onto the center of the initial membrane, very thick and tough membranes can easily be made as will be later discussed and illustrated. These final membranes are crystal clear and well formed. In this connection it may be mentioned that due to the hygroscopic nature of THF, conventional membranes sometimes are cloudy due to absorption of water from the air during drying of the conventional membrane. 3-MCH solvent eliminates this problem.

Figure 2:
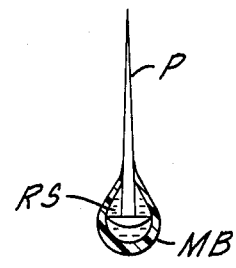

CWE devices were made in which THF and 3-MCH-based casting solutions were compared. The MCH-based CWE was superior, FIG. 2 where the element is a pin P.

Figure 3:
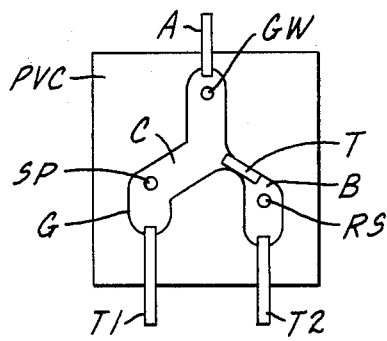

A micro ISE module for flow cells was built, FIG. 3, and tested according to the invention. The response was excellent and so were stability and reproducibility. In FIG. 3, G is a silicone gasket, GW is a grounding wire, T is a tiny Teflon tube communicating chambers B and C. A is an outlet tube which was closed while the standard reference solution was used to flush chambers C and B. The standard was inlet through tube T1 (tube A closed) and flushed into chamber B via tube T. Tube T2 leading from chamber B was open, so chamber B became filled with the reference solution. Both electrode cavities (RS, reference; SP, sample) were covered by a membrane. After this set up, T2 was closed and A opened, and the sample was run into chamber C and out tube A. The device had excellent response, there was no drift and the results were reproducible.

The disclosure was also applied to the construction of ISE microsensor chips in which the ISEs measured approximately 2 mm in diameter by 1 mm thick, formed in the shell or casing of a dual MOSFET op amp (operational amplifier) IC. This chip was an RCA CA3240 chip, FIG. 4, having eight pins and an epoxy/ceramic shell. The two cells or wells are Ca²⁺ and K⁺ ISEs, countersunk as will be explained below. Anodized silvered epoxy (SW) was the reference element.

Figure 4:
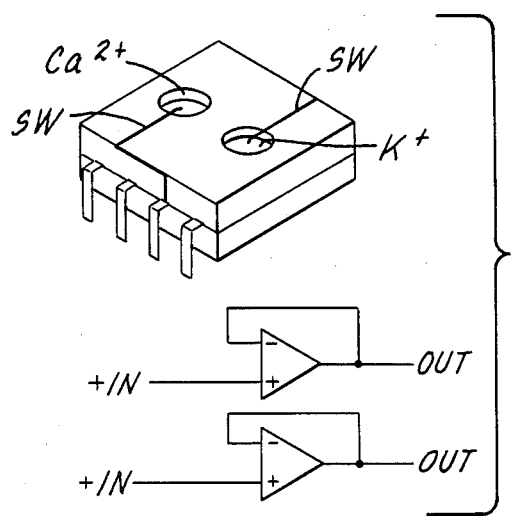

The wells, FIG. 4, were:

| Ca²⁺ Ref. Soln. | K⁺ Ref. Soln. |
|---|---|
| 4.5 g F | 4.5 g F |
| 1.13 g H₂O | 1.13 g H₂O |
| .075 g Ca/Cl₂.2H₂O (0.1 M) | .234 gm PVA |
| .234 g h.m.w. PVA | .04 gm KCl (0.1 M) |
| AgNO₃ crystal, until hazy | few AgNO₃ crystals |
| Gelled quickly and stiffly | Filled well ½ full |
| Filled well about ½ full | |
| Ca²⁺ Membrane | K⁺ Membrane |
| 1.5% ETH 1001 (6.8 mg) | 1.5% valinomycin |
| .6% NaTPB (2.5 mg) | 34% PVC |
| 34% PVC (0.15 grams) | 64.5% dioctyl adipate |
| 63.9% NPOE (0.29 grams) | 3-MCH until viscous |
| 3-MCH until viscous | |

Since one of the more important features of this invention is an internal reference solution that does not evaporate through the membrane, a shelf-life study was done. One ISE stored in air for five months and another for four months still functioned like new when immersed in a sample solution.

Figure 5:
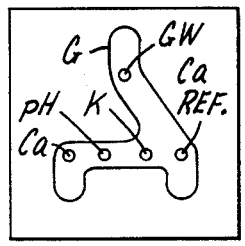

As mentioned above, one of the important advantages of micro ISE devices is their ability to be grouped into efficient arrays of multiple sensors. To test this, a multiple micro ISE module was made and tested, FIG. 5. There were three sample electrodes, Ca, pH, K and one reference electrode, Ca. The support was ¼" thick; the large diameter of each well was 7/64". Each reference element was an anodized silver wire (Ag/AgCl). This module was hooked up to a three-channel analyzer and tested out well as a flow cell analyzer.

Detailed Description of the Invention

A. Reference Elements

The internal reference element is a small diameter electrically conductive wire (e.g. 0.5 mm diam.). When a redox combination is added to the reference solution, the internal element may be either gold or platinum. This is known art.

The silver type internal reference element wire may be a silver wire per se. It may be a plastic wire coated with vapor deposited silver, a plastic wire coated with or dipped in a silver epoxy, or a plastic wire dipped in a silver ink. Preferably, the silver element is an Ag/AgCl wire, made by anodizing a silver wire in dilute hydrochloric acid resulting in a silver chloride surface. All of this is known art, deemed equivalent to an Ag/AgCl internal reference element.

B. The Reference Solution Generally

The reference solution contains the standard ion against which the sample is measured in values of electrical potential. By calibration (potential vs. concentration) the concentration of the electrolyte in the sample can be measured, as is known and practiced.

Under the present invention, the essential content of the reference solution is, by weight, about 80 to 90 percent formamide or methyl formamide (both deemed formamide herein) balance water except for 0.001 to 0.1M salt equivalent of the ion to be referenced against the sample ion. Formamide (HCONH₂) is water miscible, hygroscopic and will not evaporate through a polyvinyl chloride membrane. It is insoluble in nonpolar organics and hence will not be disadvantageously faulted by the membrane casting solution or the ionophore therein. Also, since formamide has a dielectric constant equal to or greater than 80, it will readily dissolve ions, especially the following representative ions of primary interest under the present invention:

| Cations | Anions |
|---|---|
| K⁺ | NO₃⁻ |
| Ca²⁺ | Cl⁻ |
| Ba²⁺ | ClO₄⁻ |
| Li⁺ | BF₄⁻ |
| Na⁺ | |
| Mg²⁺ | |

When the element is Ag/AgCl the reference solution contains Cl⁻ and should be saturated with AgCl, which requires only a few crystals AgNO₃.

Initial experiments had established the stability and dependability of a reference solution containing the base components, and also when a redox combination is added. However, it can be gelled with high molecular weight polyvinyl alcohol (PVA) in order to add additional ruggedness. In some, or even most, configurations PVA is not needed, as will be explained. To assure against leaching of any portion of the overcast membrane the reference solution is preferably saturated with a plasticizer and the ionophore.

Thus, for a calcium electrode a reference solution was prepared, composed of 5 grams of formamide, 1.1 grams of water and 0.031 grams of calcium chloride (0.05M), to which was added a single crystal of AgNO₃. An Ag/AgCl element was inserted into the reference solution contained in the pocket or well of an insulating support. The reference solution was sealed with a membrane and tested with accurate readouts against a sample solution containing 500 ppm CaCO₃. The reference solution, though not gelled nor otherwise modified, exhibited good long term stability after reaching equilibrium.

A potassium electrode was built and tested successfully employing a reference solution which was 18 parts by weight water and 82 parts by weight formamide, to which was added 0.05M KCl. The reference solution also contained 0.05M K₄Fe(CN)₆ and 0.05M K₃Fe(CN)₆. This solution, in a well, was covered by a membrane casting solution composed of 8 mg valinomycin (ionophore)
0.18 gm PVC
0.34 gm DOA (dioctyl adipate)

The internal (wire) element was gold. The electrode thus built was tested against a KCl solution with excellent response and slope, and good stability.

The following examples of reference solutions are preferred when using a silver electrode (Ag/AgCl or equivalent).

Example 1: Calcium Electrode (Ca²⁺)

5 grams formamide
1.3 grams H₂O
0.20 grams high molecular weight (h.m.w.) PVA
0.1M CaCl₂ (0.093 grams)
AgNO₃ crystal saturated Example 2: Potassium Electrode (K⁺)

5 grams formamide
1.3 grams H₂O
0.20 grams h.m.w. PVA
0.1M KCl (0.047 grams)

AgNO₃ crystal saturated

Example 3: Calcium Electrode 10 grams formamide
1.5 grams H₂O
0.1M CaCl₂ (0.12 grams)
AgNO₃ (1 crystal to saturate with AgCl) and saturate with ETH 1001 and o-NPOE.

This reference solution exhibited excellent conductivity.

Example 4

The best gelled reference solution (a base without addition of standard ion or AgNO₃ crystal or redox couple, wnich can be added at will) was

| Amount | % By Weight |
|---|---|
| 5 grams formamide | 79.4 |
| 1.3 grams H₂O | 20.6 |

Then add 0.26 grams high molecular weight PVA on a hot plate to make a 4% solution. This combination gels to a stiff state in a few minutes after cooling and does not absorb water.

As mentioned above, by including a plasticizer and a little of the ionophore in the reference solution, one achieves greater assurance that the components of the membrane will not penetrate the reference solution. In instances where this may be needed the amount of PVA should be reduced so the ionophore may be added before gelling occurs. The following are examples.

Example 5: Calcium Electrode 5 grams formamide
1.3 grams H₂O
0.064 grams h.m.w. PVA
0.1M CaCl₂ (0.095 grams)(1)
(1) CaCl₂ in all examples is calculated as CaCl₂

The solution was saturated with AgCl by adding one or two crystals of AgNO₃. A small amount of nitrophenyl octyl ether plasticizer (NPOE), and the calcium ionophore were added to the reference solution before filling the well and covering with the membrane casting solution.

Example 6: Potassium Electrode

This was the same as Example 5 except 0.1M KCl (0.05 grams) was substituted for the calcium ion equivalent and the ionophore-plasticizer addition was valinomycin plus DOA which is dioctyl adipate. The electrodes of Examples 5 and 6 tested satisfactorily when incorporated in module wells of 5/64" diameter, using a 1.0 mm Ag/AgCl internal element. They exhibited excellent stability and slopes. These modules were therefore set aside to test shelf life. After four months under ambient conditions there was no drift on the part of either one when subjected to the same samples as previously. Both registered good slopes and stability and good readouts were obtained even after soaking for two hours in KCl, CaCl₂ solutions.

A similar module (calcium electrode) was stored for five months and tested after soaking for five minutes in CaCl₂ solution. Its performance, response and stability were superior.

The reference solution is simply prepared by stirring the components in a vial or flask at room temperature, even when employing both an ionophore and plasticizer. If PVA is used, the formamide-water system is stirred on a hot plate with the PVA present. When the PVA dissolves, then the salt and AgNO₃ are added along with ay ionophore and plasticizer and the composition then incorporated in the well before it gels.

The Countersunk Well

Figure 6:
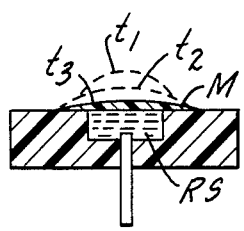

The well or cavity to contain the reference solution is tiny, of the order of 0.05" to 0.15" or so, drilled into a support of polyvinylchloride, polystyrene or polycarbonate, the reference solution being added by a micropipette. I have found that if the well is of uniform diameter, FIG. 6, a thin membrane M usually results because of little resistance to surface tension. With the progression of time ($t_1$, $t_2$, $t_3$) the membrane M may be thin and fragile, $t_3$, FIG. 6.

Figure 7:
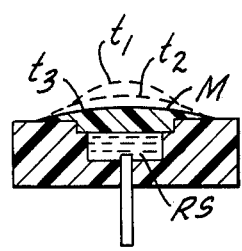

If the well is countersunk, FIG. 7, the smaller section may be filled with the reference solution, RS, whereafter the membrane casting solution is added dropwise (FIG. 7) to the upper or larger diameter section resulting in a well-formed membrane M, FIG. 7, of sturdy thickness. The increased thickness where the membrane is resident doubtless accounts for slower evaporation of the reference solution.

In most instances, use of the countersunk well eliminates the need for PVA in the reference solution.

The Membrane Generally

Under the present invention, the membrane casting solution is composed so that it can be applied directly over the reference solution without interchange of components, even if the reference solution is gelled with PVA. To accomplish this polyvinyl chloride is dissolved in a solvent which is, in effect, hydrophobic so that it will not mix with either the water or the formamide in the reference solution. I have found that 3-methylcyclohexanone (3-MCH) as a solvent for polyvinylchloride will perform this role in the membrane casting solution, effectively isolating the reference solution and the membrane to perform their respective functions, one to the exclusion of the other. Other substituted cyclic ketones such as dimethylcyclohexanone and dimethylcycloheptanone will perform the same role.

The casting solution has a density less than 1 and hence will float on the reference solution without penetrating it.

The following are preferred examples of the membrane casting solution which can be applied to form a membrane cap covering the reference solution.

Example 7: Calcium Electrode Membrane

| Amount | % by Weight |
|---|---|
| 0.29 grams o-NPOE | 63.9 |
| 0.15 grams PVC | 34 |
| 6.8 mg. ETH 1001(1) | 1.5 |
| 2.5 mg. NaTPB(2) | 0.6 |
| 3-MCH: enough to make a viscous casting solution | |

(1) calcium ionophore to transport $Ca^{2+}$
(2) sodium tetraphenyl borate; not essential but prevents other ions from interfering with the calcium ionophore

Example 8: Potassium Electrode Membrane

| Amount | % By Weight |
|---|---|
| 6.3 mg. valinomycin | 2% |

| -continued | |
|---|---|
| Amount | % By Weight |
| 0.107 grams PVC | 34% |
| 0.202 grams DOA | 64% |

To these ingredients, enough 3-MCH was added to give a thick, viscous solution which was clear and homogeneous.

Example 9: Lithium Electrode

The inner element was a 1.0 mm diameter Ag/AgCl wire. The reference solution was:
5 grams formamide
1.2 grams H$_2$O
0.07 grams h.m.w. PVA
0.1M LiCl (0.025 grams)

The reference solution was saturated (hazy solution) with AgCl and was reinforced against membrane incursion with NPOE and the lithium ionophore.

The membrane casting solution was:
7.1 mg. ETH 1644 ionophore
0.5 mg. KB(ClPh)$_4$
0.12 grams PVC
0.23 grams o-NPOE dissolved in enough 3-MCH to produce a viscous solution which was perfectly clear, producing good contact between the reference solution and the membrane casting solution. This electrode was tested against lithium sample concentrations of 0.25, 0.5 and 1.0 ppm with acceptable slopes and stability.

Most Preferred Examples

Additional experiments established the following reference solution (basis) performs exceptionally well in a 2.0 mm diameter cavity for pH, Ca$^{2+}$, Li$^+$ and K$^+$:
87% Formamide (10 grams)
13% Water (1.5 grams)

For pH: add 0.05M NaH$_2$PO$_4$/NaOH (pH 6.8) and 0.06 grams NaCl (0.1M Cl$^-$)
For Ca$^{2+}$: add 0.12 grams CaCl$_2$ (0.1M Ca$^{2+}$)
For Li$^+$ add 0.045 grams LiCl (0.1M Li$^+$)
For K$^+$: add 0.078 grams KCl (0.1M K$^+$)

The basic solution and the reference ion are mixed at room temperature and a few crystals of AgNO$_3$ are added to assure AgCl saturation evidenced by a slight haze, as usual. Optionally, but preferably, each reference solution is saturated with the ionophore and a plasticizer, the latter which may be DOA (dioctyladipate) or DOS (dioctylsebacate) or o-NPOE (ortho nitro phenyl octyl ether) or 2-ethylhexyl sebacate as each performs as an equivalent of the other.

The ionophore is not always named in the present examples as they are well known including:

| Ion | Ionophore |
|---|---|
| Ca$^{2+}$ | ETH 1001 |
| K$^+$ | valinomycin |
| Na$^+$ | ETH 227 |
| Li$^+$ | ETH 1644 |
| pH | tridodecylamine |

The ionophore will be about 2% by weight of the membrane casting solution. I have determined the following membrane casting solution to perform satisfactorily with any of the reference solutions under this heading:

34% PVC (0.107 grams)
64% DOA (0.202 grams)
2% ionophore (e.g. 6.3 mg. valinomycin)

In preparing the membranes all components are dissolved in enough 3-MCH to produce a viscous solution.

A K$^+$ membrane does not require KB(ClPh)$_4$ but all others (e.g. Ca$^{2+}$, Li$^+$) preferably incorporate it or NaTPB.

FIG. 8

This partly diagrammatic figure shows, in section, one of the more important electrode configurations comprising three essential parts: (1) a PVC (or equivalent) sensor base or module denoted SB (⅛" thick) containing the reference and sample electrode respectively denoted RS and SP (1.6 mm diam.) each having a 0.50 mm (diam.) Ag/AgCl wire, together with a copper grounding wire denoted GW; (2) an (8 pin) DIP socket, denoted ST, which will be wired for the standard dual FET op amp device; and (3) a PVC tube denoted TB (e.g. 2 mm. I.D.) to conduct the sample left to right across the electrode membranes. The sensitivity was remarkable: 1 millivolt resolution and a (plus-minus) accuracy of 0.5%.

Figure 8:
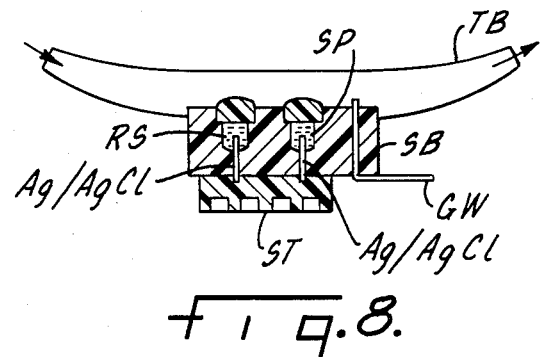

Only two sensor cells are shown in FIG. 8 (e.g. Ca$^{2+}$ and K$^+$) but four in-line sensors in a similar, enlarged configuration were successfully tested: K$^+$ (ref), Li$^+$, pH and Ca$^{2+}$ as can be appreciated from FIG. 5.

Figure 9:
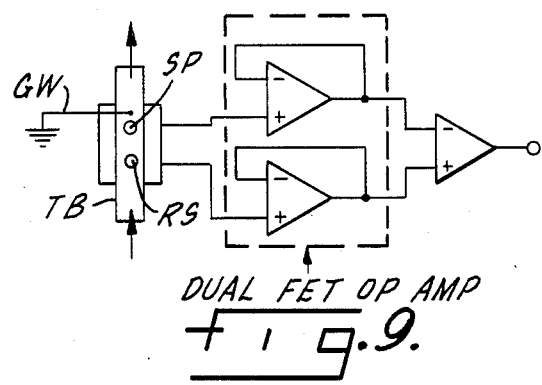

Due to the high electrical impedance of these ion sensitive sensors, dual FET ("field effect transistor") op amps (or dual MOSFET op amps) may be connected in a voltage follower configuration directly to the Ag/AgCl elements of the microelectrodes (FIG. 9) to perform the impedance transformation. The potential difference between the reference and sample sensors may thus be obtained using an intrumentation amplifier, FIG. 9. The ground wire is needed to prevent the circuit from saturating.

Electrode Stability

An electrode is "stable" over a given time period if it produces the same potential for a given activity of nalyte ion. Analyte ion is defined as the ion that is to be measured by an electrode.

To test for electrode stability, an electrode is immersed in a standard analyte concentration and the potential recorded. The value of the potential is repeatedly recorded over a given period of time (e.g., weeks, months, etc.) and any change noted. Drift rate equals change in potential divided by the time period (e.g., 2 mV/day, etc.).

Testing for Performance

Several well known test procedures were used:
1. Continuous Dilution:

A known standard of analyte ion is continuously diluted at a constant, known rate with a solution containing no analyte ion. The analyte ion concentration at the electrode at any time can be calculated by an exponential equation. If the electrode is functioning properly, the electrode will respond with a sensitivity given by the Nernst equation:

$$\frac{59.6 \text{ mV}}{Z} \text{ per decade activity change.}$$
where $Z$ = ion charge.

2. Serial Standards:

Electrode is immersed in a series of solutions containing known concentrations of analyte ion. Sensitivity should equal Nernst slope.

3. Standard Addition/Dilution:

This is a well known method involving spiking an unknown sample containing the analyte ion with a known amount of analyte ion and then performing a known dilution. The analyte concentration can readily be calculated from a commonly employed formula.

Ionophore Chemistry

ETH1001: N,N'-di [(11-ethoxycarbonyl) undecyl]-N,N'-4,5 - tetramethyl-3,6-dioxaoctane diamide ETH227: N,N',N''- triheptyl - N,N',N''- trimethyl - 4,4',4''- propylidynetris (3-oxabutyramide)

ETH1644: N,N,N'',N'''- tetraisobutyl-cis-cyclohexane-1,2 - dicarboxamide

Hence while preferred embodiments and the chemistry of the invention have been disclosed, it is to be understood that changes and modifications may be adopted without departing from equivalent practice.

I claim:

1. In an ion selective electrode having a support with a cavity therein containing an aqueous reference solution, sensitive to the concentration of external sample ions, and having either an Ag/AgCl reference element immersed in the reference solution or an inert metal internal reference element immersed in an aqueous reference solution containing a redox couple the improvement wherein:

said aqueous reference solution containing formamide and a concentration of the ion to be measured; and an ion permeable membrane cast on to and set over said reference solution, said membrane being cast, from polyvinyl chloride in a water insoluble solvent and containing an ionophore having the role of transporting the external ion through the membrane into the reference solution.

2. Electrode according to claim 1 in which the reference solution is gelled with polyvinyl alcohol.

3. Electrode according to claim 1 in which the formamide-to-water ratio is about 80/20 to 90/10 by weight.

4. Electrode according to claim 1 in which the electrode is Ag/AgCl, and in which the reference solution contains about 0.001 to 0.1M quantity of a salt presenting the standard ion.

5. Electrode according to claim 1 in which the membrane casting solution has a density less than 1.

6. Electrode according to claim 1 in which reference solution is contained in a countersunk cavity.

7. Electrode according to claim 6 in which the countersunk cavity is formed in a support having the components of an operational amplifier.

8. Electrode according to claim 1 in which the reference solution contains an ionophore along with a plasticizer to reduce leaching of the membrane components into the reference solution.

9. Electrode according to claim 1 in which the support has several cavities containing separate quantities of the reference solution respectively containing different ion standards.

10. Method of manufacturing an ion selective electrode for detecting an external ion including the steps of selecting a support with a cavity therein, positioning in the cavity one end of an electrically conductive reference electrode, depositing in the cavity an aqueous reference solution containing formamide and an amount of the ion to be measured; and covering the reference solution with an ion permeable membrane constituted by polyvinyl chloride in a water insoluble solvent and containing an ionophore having the role of transporting the external ion through the membrane into the reference solution.

11. Method according to claim 10 including the step of gelling the reference solution with polyvinyl alcohol.

12. Method according to claim 10 in which the ratio of formamide-to-water ratio is adjusted to be about 80/20 to 90/10 by weight.

13. Method according to claim 10 in which the electrode is chosen, as Ag/AgCl, and in which the reference solution contains about 0.001 to 0.1M quantity of a salt presenting the external ion.

14. Method according to claim 10 in which the membrane has a density less than 1.

15. Method according to claim 10 including the step of selecting a support in which the cavity is a countersunk cavity.

16. Method according to claim 10 including the step of adding to the reference solution an ionophore along with a plasticizer to reduce leaching of the membrane components into the reference solution.

17. Method according to claim 10 including the steps of selecting a support having several cavities therein, and depositing in each cavity a portion of said aqueous reference solution which portions have different standard ions.

18. Method according to claim 10 including the step of selecting an operational amplifier as the support.

* * * * *

UNITED STATES PATENT AND TRADEMARK OFFICE
CERTIFICATE OF CORRECTION

PATENT NO. : 4,814,060

DATED : March 21, 1989

INVENTOR(S) : Rodney H. Banks

It is certified that error appears in the above—identified patent and that said Letters Patent is hereby corrected as shown below:

Col. 11, Claim 1, line 11, change "containing" to --contains--

Signed and Sealed this

Twelfth Day of September, 1989

Attest:

DONALD J. QUIGG

Attesting Officer

Commissioner of Patents and Trademarks